United States Patent [19]

Schloesser et al.

[11] Patent Number: 5,571,898
[45] Date of Patent: Nov. 5, 1996

[54] BASIC DYES BASED ON AMIDES OF J-ACID (1-HYDROXY-6-AMINONAPHTHALENE-3-SULFONIC ACID) AND AMIDES OF J-ACID

[75] Inventors: Ulrike Schloesser, Ludwigshafen; Udo Mayer, Frankenthal, both of Germany

[73] Assignee: BASF Aktiengesellschaft, Ludwigshafen, Germany

[21] Appl. No.: 500,565

[22] Filed: Jul. 11, 1995

Related U.S. Application Data

[63] Continuation of Ser. No. 215,647, Mar. 22, 1994, abandoned, which is a continuation-in-part of Ser. No. 136,034, Oct. 14, 1993, abandoned.

[30] Foreign Application Priority Data

Oct. 19, 1992 [DE] Germany .......................... 42 35 154.5

[51] Int. Cl.$^6$ .................... C09B 29/15; C09B 31/068; D06P 1/41; D21H 21/28
[52] U.S. Cl. .................... 534/604; 534/592; 534/605; 534/614; 534/615; 534/641; 534/797; 534/798; 534/799; 534/829; 534/872; 534/873; 534/878; 8/437; 8/654; 8/694; 8/919; 8/924; 8/927; 162/162
[58] Field of Search .................... 534/592, 604, 534/614, 615, 641, 797–799, 829, 872, 873, 878; 8/437, 654, 694, 919, 924, 927; 162/162

[56] References Cited

U.S. PATENT DOCUMENTS

| | | | |
|---|---|---|---|
| 1,903,599 | 4/1933 | Schweitzer et al. | 534/878 X |
| 2,817,655 | 12/1957 | Schetty et al. | 534/641 X |
| 3,067,191 | 12/1962 | Meller et al. | 534/641 X |
| 3,096,322 | 7/1963 | Straley et al. | 534/641 X |
| 3,403,143 | 9/1968 | Ramanathan | 534/615 X |
| 3,524,842 | 8/1970 | Grossmann et al. | 534/615 X |
| 4,273,707 | 6/1981 | Pedrazzi | 534/872 X |
| 4,363,761 | 12/1982 | Pedrazzi . | |
| 4,767,175 | 8/1988 | Doré et al. | 534/614 X |
| 4,839,468 | 6/1989 | Nickel et al. | 534/604 |
| 4,935,499 | 6/1990 | Ruske et al. | 534/605 |
| 4,975,118 | 12/1990 | Mayer | 534/604 |
| 5,144,064 | 9/1992 | Hahn et al. | 562/49 |
| 5,354,904 | 10/1994 | Mayer et al. | 534/878 X |

FOREIGN PATENT DOCUMENTS

| | | |
|---|---|---|
| 600169 | 6/1960 | Canada .................... 534/592 |
| 62824 | 10/1982 | European Pat. Off. . |
| 176195 | 4/1986 | European Pat. Off. . |
| 212553 | 3/1987 | European Pat. Off. . |
| 537535 | 4/1993 | European Pat. Off. . |
| 2724079 | 12/1978 | Germany . |
| 803525 | 10/1958 | United Kingdom .................... 534/592 |
| 1097627 | 1/1968 | United Kingdom .................... 534/604 |
| 1586411 | 3/1981 | United Kingdom . |

OTHER PUBLICATIONS

*Roempps Chemic–Lexikon*, p. 3438. (1988)**.
W. König et al. *J. Prakt. Chem.*, vol. 101, pp. 38–57, Jun. 11, 1920.**

*Primary Examiner*—Fiona T. Powers
*Attorney, Agent, or Firm*—Oblon, Spivak, McClelland, Maier & Neustadt, P.C.

[57] ABSTRACT

There are described dyes of the formula

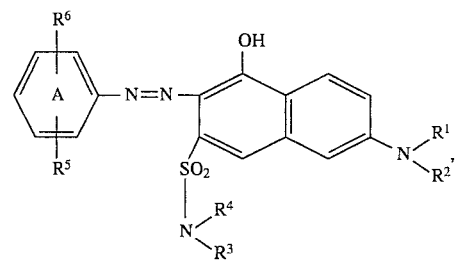

where the ring A may be benzofused, $R^1$ is substituted or unsubstituted $C_1$-$C_{13}$-alkyl, substituted or unsubstituted phenyl, $C_1$-$C_8$-alkanoyl, substituted or unsubstituted benzoyl, substituted $C_2$-$C_4$-alkanoyl, or substituted diaminotriazinyl, $R^2$ is hydrogen or $C_1$-$C_4$-alkyl or $R^1$ and $R^2$ together with the nitrogen atom joining them together are a heterocyclic radical, $R^3$ and $R^4$ are each substituted or unsubstituted $C_1$-$C_{13}$-alkyl, substituted or unsubstituted $C_5$-$C_7$-cycloalkyl or substituted or unsubstituted piperidinyl and $R^3$ may also be hydrogen, $R^5$ is hydrogen, $C_1$-$C_4$-alkyl, $C_1$-$C_4$-alkoxy, $C_2$-$C_5$-alkanoylamino, halogen, nitro, cyano, substituted or unsubstituted phenylazo, $C_2$-$C_4$-alkanoylamino substituted by a quaternizable or quaternary group, or $C_2$-$C_4$-alkoxy, $C_2$-$C_4$-alkoxycarbonyl or $C_2$-$C_4$-alkoxycarbamoyl which are each substituted by a quaternizable or quaternary group, and $R^6$ is hydrogen, $C_1$-$C_4$-alkyl, $C_1$-$C_4$-alkoxy, halogen, nitro or cyano,
with the proviso that at least one quaternizable or quaternary group is present in the molecule, the use thereof for dyeing or printing polymeric material, and novel amides of J-acid.

5 Claims, No Drawings

BASIC DYES BASED ON AMIDES OF J-ACID (1-HYDROXY-6-AMINONAPHTHALENE-3-SULFONIC ACID) AND AMIDES OF J-ACID

This application is a continuation of application Ser. No. 08/215,647, filed on Mar. 22, 1994, now abandoned, which is a continuation-in-part of application Ser. No. 08/136,034, filed on Oct. 14, 1993, now abandoned.

The present invention relates to novel dyes of the formula I

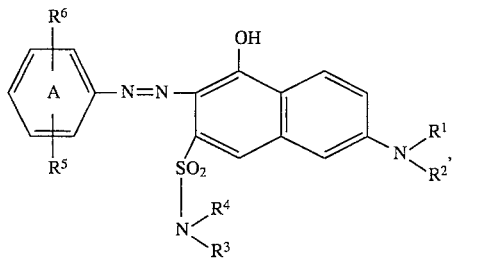

where the ring A may be benzofused, $R^1$ $C_1$-$C_{13}$-alkyl, benzyl, 2-chloroethyl, substituted or unsubstituted phenyl, $C_1$-$C_8$-alkanoyl, substituted or unsubstituted benzoyl or a radical of the formula

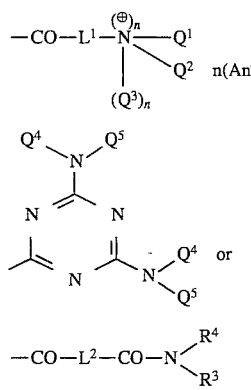

where $L^1$ is $C_1$-$C_3$-alkylene, $L^2$ is $C_2$-$C_3$-alkylene, which may be chlorine-substituted, vinylene or phenylene, n is 0 or 1, $Q^1$, $Q^2$ and $Q^3$ are identical or different and each is independently of the others hydrogen or unsubstituted or hydroxyl-substituted $C_1$-$C_8$-alkyl, which may be interrupted by from 1 to 3 oxygen atoms in ether function or by from 1 to 3 imino groups which may be substituted by $C_1$-$C_4$-alkyl or ω-hydroxy-$C_1$-$C_8$-alkyl, which may be interrupted by from 1 to 3 oxygen atoms in ether function, or $Q^1$ and $Q^2$, together with the nitrogen atom joining them together, are a 5- or 6-membered saturated or unsaturated heterocyclic radical which may contain a further hetero atom selected from the group consisting of nitrogen, oxygen and sulfur, and $An^{\ominus}$ is the equivalent of an anion, and $Q^4$ and $Q^5$ are identical or different and each is independently of the other $C_1$-$C_{13}$-alkyl, which may be interrupted by from 1 to 4 oxygen atoms in ether function, by imino or by $C_1$-$C_4$-alkylimino groups and may be substituted by amino, by a 5- or 6-membered saturated or unsaturated heterocyclic radical which contains a nitrogen atom and may contain a further hereto atom selected from the group consisting of nitrogen, oxygen and sulfur, or by substituted or unsubstituted $C_5$-$C_7$-cycloalkyl, substituted or unsubstituted phenyl, substituted or unsubstituted $C_5$-$C_7$-cycloalkyl or unsubstituted or $C_1$-$C_4$-alkyl-substituted piperidinyl, and $Q^4$ may also be hydrogen, $R^2$ is hydrogen or $C_1$-$C_4$-alkyl or $R^1$ and $R^2$ together are a radical of the formula CO—$L^3$, where $L^3$ is $C_3$-$C_4$-alkylene, $R^3$ and $R^4$ are identical or different and each is independently of the other $C_1$-$C_{13}$-alkyl, which may be interrupted by from 1 to 4 oxygen atoms in ether function or by from 1 to 4 imino groups which may be substituted by $C_1$-$C_4$-alkyl or ω-hydroxy-$C_1$-$C_8$-alkyl, which may be interrupted by from 1 to 3 oxygen atoms in ether function, and may be substituted by hydroxyl, by amino, by a 5- or 6-membered saturated or unsaturated heterocyclic radical which contains a nitrogen atom and may contain a further hetero atom selected from the group consisting of nitrogen, oxygen and sulfur, or by substituted or unsubstituted $C_5$-$C_7$-cycloalkyl, substituted or unsubstituted phenyl, substituted or unsubstituted $C_5$-$C_7$-cycloalkyl or unsubstituted or $C_1$-$C_4$-alkyl-substituted piperidinyl, and $R^3$ may also be hydrogen, and $R^3$ and $R^4$, together with the nitrogen atom joining them together, are a 5- or 6-membered saturated heterocyclic radical which may contain a further hetero atom selected from the group consisting of oxygen and sulfur, $R^5$ is hydrogen, $C_1$-$C_4$-alkyl, $C_1$-$C_4$-alkoxy, $C_2$-$C_5$-alkanoylamino, halogen, nitro, cyano, unsubstituted or $C_1$-$C_4$-alkyl-substituted phenylazo or a radical of the formula

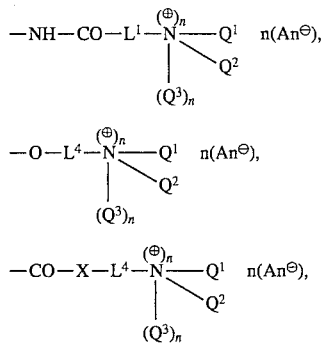

where X is oxygen or imino, and $L^4$ is $C_2$-$C_4$-alkylene, and $Q^1$, $Q^2$, $Q^3$, n and $An^{\ominus}$ are each as defined above, and $R^6$ is hydrogen, $C_1$-$C_4$-alkyl, $C_1$-$C_4$-alkoxy, halogen, nitro or cyano, with the proviso that at least one quaternizable or quaternary group is present in the molecule, the use thereof for dyeing or printing polymeric material, and novel amides of J-acid.

It is an object of the present invention to provide novel basic azodyes having a coupling component of the series of the amides of J-acid (1-hydroxy-6-aminonaphthalene-3-sulfonic acid). The novel dyes shall be advantageous for dyeing or printing polymeric material, in particular paper. The dyeings obtained shall have good in-use/service properties.

We have found that this object is achieved by the dyes of the formula I defined at the beginning.

Any alkyl or alkylene appearing in the abovementioned formula may be straight-chain or branched.

Any substituted phenyl appearing in the abovementioned formula may have as substituents for example $C_1$-$C_4$-alkyl, $C_1$-$C_4$-alkoxy or halogen, in particular chlorine or bromine.

The number of substituents in substituted phenyl is in general from 1 to 3.

Any substituted $C_5$-$C_7$-cycloalkyl appearing in the abovementioned formula may have as substituents for example $C_1$-$C_4$-alkyl or $C_1$-$C_4$-aminoalkyl, in which case cycloalkyl is in general substituted by from 1 to 3 alkyl groups and/or a single aminoalkyl group.

Any $C_1$-$C_4$-alkyl-substituted piperidinyl appearing in the abovementioned formula has in general from 1 to 4 $C_1$-$C_4$-alkyl groups, in particular methyl groups, substituted 4-piperidinyl being preferred.

A $C_1$-$C_{13}$-alkyl $R^3$, $R^4$, $Q^4$ or $Q^5$ which is substituted by a 5- or 6-membered heterocyclic radical which contains a nitrogen atom and may contain a further hereto atom selected from the group consisting of nitrogen, oxygen and sulfur, suitable substituents are saturated or unsaturated radicals, such as pyrrolidinyl, piperidinyl, morpholinyl, thiomorpholinyl, piperazinyl, N-($C_1$-$C_4$-alkyl)piperazinyl, pyrrolyl, pyrazolyl, imidazolyl, oxazolyl, isooxazolyl, thiazolyl or isothiazolyl.

$Q^1$ combined with $Q^2$ and the nitrogen atom joining them together to form a 5- or 6-membered heterocyclic radical can also be one of these radicals.

$R^3$ combined with $R^4$ and the nitrogen atom joining them together to form a 5 - or 6-membered saturated heterocyclic radical which may contain a further hetero atom selected from the group consisting of nitrogen, oxygen and sulfur can be for example pyrrolidinyl, piperidinyl, morpholinyl, thiomorpholinyl, piperazinyl or N-($C_1$-$C_4$-alkyl)piperazinyl.

Any substituted alkyl appearing in the abovementioned formula contains in general one or two substituents.

$R^1$, $R^2$, $R^3$, $R^4$, $R^5$, $R^6$, $Q^1$, $Q^2$, $Q^3$, $Q^4$ and $Q^5$ are each for example methyl, ethyl, propyl, isopropyl, butyl, isobutyl, sec-butyl or tert-butyl.

$R^1$, $R^3$, $R^4$, $Q^1$, $Q^2$, $Q^3$, $Q^4$ and $Q^5$ may each also be for example pentyl, isopentyl, neopentyl, tert-pentyl, hexyl, 2-methylpentyl, heptyl, octyl, 2-ethylhexyl or isooctyl.

$R^1$, $R^3$, $R^4$, $Q^4$ and $Q^5$ may each also be for example nonyl, isononyl, decyl, isodecyl, undecyl, dodecyl, tridecyl, 3,5,5,7- tetramethylnonyl, isotridecyl (the above designations isooctyl, isononyl, isodecyl and isotridecyl are trivial names derived from the oxo process alcohols—cf. Ullmanns Encyklopädie der technischen Chemie, 4th Edition, Volume 7, pages 215 to 217, and Volume 11, pages 435 and 436), benzyl, 1- or 2-phenylethyl, phenyl, 2-, 3- or 4-methylphenyl, 2,4-dimethylphenyl, 2-, 3- or 4-methoxyphenyl, 2,4-dimethoxyphenyl, 2-, 3- or 4-chlorophenyl or 2,4-dichlorophenyl.

$R^1$ may also be for example formyl, acetyl, propionyl, butyryl, isobutyryl, pentanoyl, hexanoyl, heptanoyl, octanoyl, 2-ethylhexanoyl, benzoyl, 2-, 3- or 4-methylbenzoyl, 2,4-dimethylbenzoyl, 2-, 3- or 4-methoxybenzoyl, 2,4-dimethoxybenzoyl, 2-, 3- or 4-chlorobenzoyl or 2,4-dichlorobenzoyl.

$R^3$, $R^4$, $Q^4$ and $Q^5$ may each also be for example 2-aminoethyl, 2- or 3-aminopropyl, 2- or 4-aminobutyl, 5-aminopentyl, 6- aminohexyl, 7- aminoheptyl, 8- aminooctyl, 3-aza-3-methylbutyl, 4-aza-4-methylpentyl, 3-aza-3-ethylpentyl, 4-aza-4-ethylhexyl, 5-amino-3-azapentyl, 6-amino-3-azahexyl, 6-amino-4-azahexyl, 7-amino-4-azaheptyl, 8-amino-3,6-diazaoctyl, 3-aminoprop-2-yl, 8-amino-4-(2-aminoethyl)octyl, 2-(pyrrolidin-1-yl)ethyl, 2-or 3-(pyrrolidin-1-yl) propyl, 2-(piperidin-1-yl)ethyl, 2- or 3-(piperidin-1-yl)propyl, 2-(morpholin-4-yl)ethyl, 2- or 3-(morpholin-4-yl)propyl, 2-(piperazin-1-yl)ethyl, 2- or 3-(piperazin-1-yl) propyl, 2-(4-methylpiperazin-1-yl)ethyl, 2- or 3-(4-methylpiperazin-1-yl)propyl, 2-(imidazol-1-yl)ethyl, 2- or 3-(imidazol-1-yl)propyl, cyclopentyl, cyclohexyl, cycloheptyl, 3-aminomethyl- 3,5,5-trimethylcyclohexyl or 2,2,6,6-tetramethylpiperidin- 4-yl.

$R^3$, $R^4$, $Q^1$, $Q^2$, $Q^3$, $Q^4$ and $Q^5$ may each also be for example 2-methoxyethyl, 2-ethoxyethyl, 2-propoxyethyl, 2-isopropoxyethyl, 2-butoxyethyl, 2- or 3-methoxypropyl, 2- or 3-ethoxypropyl, 2- or 3-propoxypropyl, 2- or 3-butoxypropyl, 2- or 4-methoxybutyl, 2- or 4-ethoxybutyl, 2- or 4-propoxybutyl, 3,6-dioxaheptyl, 3,6-dioxyoctyl, 4,8-dioxanonyl, 3,7-dioxaoctyl, 3,7-dioxanonyl, 4,7-dioxaoctyl, 4,7-dioxanonyl, 2- or 4-butoxybutyl, 4,8-dioxadecyl, 3,6,9-trioxadecyl or 3,6,9-trioxaundecyl.

$R^3$, $R^4$, $Q^4$ and $Q^5$ may each also be for example 3,6,9-trioxadodecyl, 3,6,9,12-tetraoxatridecyl or 3,6,9,12-tetraoxatetradecyl.

$R^3$, $R^4$, $Q^1$, $Q^2$ and $Q^3$ may each also be for example 4-hydroxy-2-methyl-3-azabutyl, 4-hydroxy-3-hydroxymethyl-2-methyl-3-azabutyl, 5-hydroxy- 2-methyl-3-azapentyl, 5-hydroxy-3-(2-hydroxyethyl)-2-methyl-3-azapentyl, 8-hydroxy-2-methyl-3-aza-6-oxaoctyl, 11-hydroxy-2-methyl-3-aza-6,9-dioxaundecyl, 8-hydroxy-3-(5-hydroxy-3-oxapentyl)-2-methyl-3-aza-6-oxaoctyl, 11-hydroxy-3-(8-hydroxy- 3,6-dioxaoctyl)-2-methyl-3-aza-6,9-dioxaundecyl, 2-hydroxyethyl, 2- or 3-hydroxyethyl or 2- or 4-hydroxybutyl.

$R^5$ and $R^6$ may each also be for example methoxy, ethoxy, propoxy, isopropoxy, butoxy, isobutoxy, sec-butoxy, fluorine, chlorine or bromine.

$R^5$ may also be for example acetylamino, propionylamino, butyrylamino, isobutyrylamino, pentanoylamino, phenylazo or 2-, 3- or 4-methylphenylazo.

$L^1$ is for example methylene, ethylene or 1,2- or 1,3-propylene.

$L^2$ is for example ethylene, 1,2- or 1,3-propylene, chloroethylene or chloro-1,2- or -1,3-propylene.

$L^3$ is for example 1,2- or 1,3-propylene or 1,2-, 2,3- or 1,4-butylene.

$L^4$ is for example ethylene, 1,2- or 1,3-propylene, 1,2-, 2,3- or 1,4-butylene.

The equivalent $An^\ominus$ of an anion is derived for example from the following anions: fluoride, chloride, bromide, iodide, phosphate, hydrogen phosphate, dihydrogen phosphate, formate, acetate, propionate, mono-, di- or trichloroacetate, lactate, methoxyacetate, citrate, succinate, methanesulfonate, benzenesulfonate, 2- or 4-methylbenzenesulfonate or naphthalenesulfonate.

Preference is given to dyes of the formula I where $R^1$ is $C_2$-$C_4$-alkanoyl, benzoyl or a radical of the formula

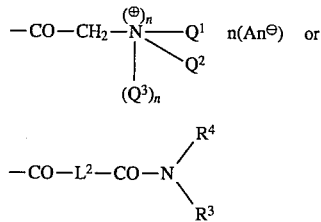

where $L^2$, $Q^1$, $Q^2$, $Q^3$, $R^3$, $R^4$, $An^\ominus$ and n are each as defined above and $R^2$ is hydrogen, $C_1$-$C_4$- alkyl or phenyl.

Preference is further given to dyes of the formula I where $R^3$ is hydrogen and $R^4$ is $C_1$-$C_{13}$-alkyl which is interrupted by 1 or 2 oxygen atoms in ether function, by imino or $C_1$-$C_4$-alkylimino groups and/or substituted by amino or by a 5- or 6-membered saturated or unsaturated heterocyclic radical which contains one or two nitrogen atoms.

Particular preference is given to dyes of the formula I where $R^1$ is acetyl.

Preference is further given to dyes of the formula I where $R^5$ is $C_1$-$C_4$-alkyl, $C_1$-$C_4$-alkoxy, $C_2$-$C_4$-alkanoylamino or phenylazo and $R^6$ is hydrogen.

The novel basic azo dyes of the formula I can be obtained in a conventional manner.

One option is for example to diazotize an aniline of the formula II

where $R^5$, $R^6$ and the ring A are each as defined above, in a conventional magnet and couple it with a naphthalene derivative of the formula III

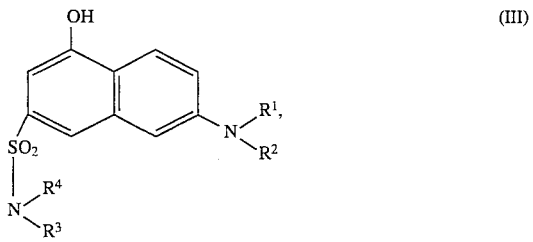

where $R^1$, $R^2$, $R^3$ and $R^4$ are each as defined above.

Those dyes of the formula I which contain a quaternary radical are advantageously obtained by first preparing the neutral azo dye and then quaternizing it with a $C_2$-$C_4$-alkylene oxide or with a compound of the formula IV

$$Q^6—Y \qquad (IV),$$

where $Q^6$ is unsubstituted or hydroxyl-substituted $C_1$-$C_4$-alkyl and Y is a leaving group, for example chloride, bromide, iodide, methosulfate, ethosulfate, benzenesulfonate or 2- or 4-methylbenzenesulfonate.

Some of the naphthalene derivatives of the formula III are known per se; see for example EP-A-537 535.

The basic azo dyes of the formula I according to the invention can be used alone, mixed with one another or mixed with other cationic or anionic compounds in the form of their solutions or in the form of powders or granules. They are advantageous for dyeing or printing polymeric material, in particular paper stock, but also cellulose, cotton, leather, bast fibers, hemp, flax, sisal, jute, coir or straw.

For the preparation of formulations of the novel dyes of the formula I attention must be drawn in particular to the use of polymers such as polyacrylic acids, polyacrylic acid derivatives, polyvinylamines, polyvinylamides, polyvinyl acetates, polyvinyl alcohols, polyvinylpyrrolidones, polysiloxanes or copolymers of the respective monomers. It is similarly possible to use oligomers of ethyleneimine, ethylene oxide or propylene oxide or derivatives thereof. Also of great importance are N-alkylated pyrrolidones or N-(2-hydroxyethyl)pyrrolidones.

The dyes are preferably usable in the production of pulp-colored, sized or unsized paper. They can likewise be used for coloring paper by the dip method.

The dyeing of paper, leather or cellulose is effected in a conventional manner.

The novel dyes or formulations thereof cause virtually no, if any, staining of the waste water from papermaking, which is particularly favorable for keeping water courses clean. They are highly substantive, do not marble when applied to paper, and are substantially pH-insensitive. The dyeings on paper are notable for good lightfastness. On prolonged exposure to light the shade changes on-tone. The dyes according to the invention also have good solubility.

The dyed paper, which is readily bleachable, is wet-fast, not only to water but also to milk, liquid soap, sodium chloride solutions, fruit juices or sweetened mineral water and, owing to its good alcohol fastness, is also fast to alcoholic beverages.

The novel dyes can also be used for dyeing, padding or printing polyacrylonitrile textiles or anionically modified polyamide or polyester textiles.

The present invention further provides novel sulfonamides of the formula IIIa

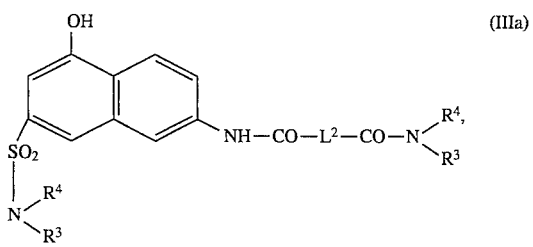

where $L^2$ is $C_2$-$C_3$-alkylene, which may be chlorine-substituted, vinylene or 1,2-phenylene and $R^3$ and $R^4$ are identical or different and each is independently of the other $C_1$-$C_{13}$-alkyl, which may be interrupted by from 1 to 4 oxygen atoms in ether function or by from 1 to 4 imino groups which may be substituted by $C_1$-$C_4$-alkyl or ω-hydroxy-$C_1$-$C_8$-alkyl, which may be interrupted by from 1 to 3 oxygen atoms in ether function, and may be substituted by hydroxyl, by amino, by a 5- or 6-membered saturated or unsaturated heterocyclic radical which contains a nitrogen atom and may contain a further hereto atom selected from the group consisting of nitrogen, oxygen and sulfur, or by substituted or unsubstituted $C_5$-$C_7$-cycloalkyl, substituted or unsubstituted phenyl, substituted or unsubstituted $C_5$-$C_7$-cycloalkyl or unsubstituted or $C_1$-$C_4$-alkyl-substituted piperidinyl, and $R^3$ may also be hydrogen, and $R^3$ and $R^4$, together with the nitrogen atom joining them together, are a 5- or 6-membered saturated heterocyclic radical which may contain a further hereto atom selected from the group consisting of oxygen and sulfur, with the proviso that at least one quaternizable group is present in the molecule.

Preference is given to those sulfonamides of the formula IIIa where $R^3$ is hydrogen and $R^4$ is $C_1$-$C_{13}$-alkyl which has at least one quaternizable nitrogen atom.

The novel sulfonamides of the formula IIIa can be obtained for example by reacting J-acid with cyclic carboxylic anhydrides of the formula V

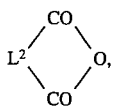

(V)

where $L^2$ is as defined above, treating the resulting reaction mixture with an appropriate halogenating reagent, eg. phosphoryl chloride, to convert the sulfonic acid group into a halosulfonyl group eg. a chlorosulfonyl group, and then reacting with an amine of the formula VI

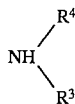

(VI)

where $R^3$ and $R^4$ are each as defined above.

The sulfonamides of the invention are useful intermediates for synthesizing the dyes of the formula I.

Embodiments of the invention will now be more particularly described by way of example. Percentages are by weight.

EXAMPLE 1

30 g of 1,2-diaminopropane were admixed at 20° C. with 8.5 g (0.025 mol) of N-acetyl-J-acid chloride, and the mixture was stirred at room temperature for 60 h. The resulting oil was diluted with 200 ml of water, adjusted to pH 8 with hydrochloric acid, and admixed at pH 7.5–8 with 3.75 g (0.025 mol) of diazotized p-aminoacetanilide. The pH was kept constant with aqueous sodium carbonate solution.

The solution of the diazonium salt was prepared as follows: 3.75 g (0.025 mol) of p-aminoacetanilide were stirred at 0°–3° C. with 50 ml of water and 12.5 ml of 30% strength by weight hydrochloric acid over 30 min and then admixed with 65 g of ice. The diazotization was carried out by the dropwise addition of 7.5 ml of 23% strength by weight aqueous sodium nitrite solution. The reaction mixture was stirred at 0°–3° C. for a further 2 h and then used for the coupling reaction.

Filtration with suction and drying yielded 9.5 g (76%) of the dye of the formula

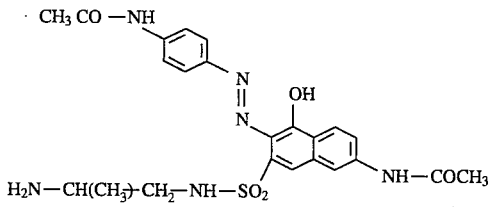

$\lambda$max: 502 nm (in 85% strength by weight acetic acid)

EXAMPLE 2

3.08 g (0.025 mol) of o-anisidine were dissolved in 50 ml of water and 7 ml of 38% strength by weight hydrochloric acid and admixed at 0° C. with 17.3 ml of 10% strength by weight aqueous sodium nitrite solution, and the mixture was stirred at 0° C. for a further 20 min and clarified with active charcoal. The resulting solution of the diazonium salt was reacted with an equimolar amount of sulfonamide as described in Example 1.

The dye of the formula

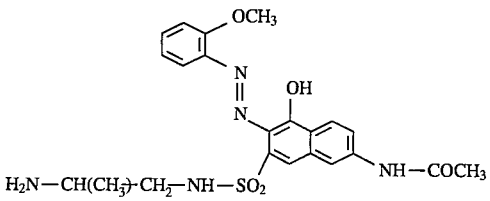

was isolated in a 62% yield (14.4 g). $\lambda$max: 501 nm (in 85% strength by weight acetic acid)

EXAMPLE 3

8.5 g (0,025 mol) of N-acetyl-J-acid chloride were added at 20° C. to 30 g of N,N-dimethylethylenediamine and the mixture was stirred at room temperature for 60 h. The resulting oil was diluted with 200 ml of water, brought to pH 8 with hydrochloric acid and coupled at pH 7.5–8 with 4.93 g (0.025 mol) of diazotized p-aminobenzene. The pH was kept constant with aqueous sodium carbonate solution.

Preparation of the diazonium salt of p-aminobenzene: 4.93 g (0.025 mol) of p-aminobenzene were dissolved in 30 ml of water and 10 ml of 30% strength by weight hydrochloric acid, the mixture was stirred at room temperature for 15 min, was admixed with 150 g of ice-water and at 15° C. all at once with 7.5 ml of 23% strength by weight aqueous sodium nitrite solution, stirred at 15° C. for a further 2 h and then clarified.

The resulting solution of the diazonium salt was reacted with an equimolar amount of sulfonamide as described in Example 1.

Filtration with suction and drying yielded 19.4 g (70%) of the dye of the formula

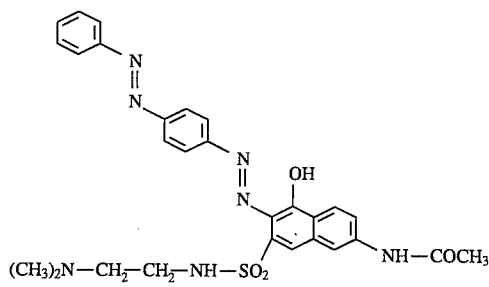

$\lambda$max: 506 nm (in 85% strength by weight acetic acid)

The same method gives the dyes of the formula

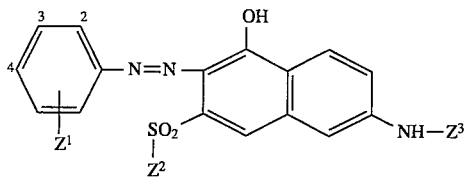

listed below in Table 1.

TABLE

| Ex. No. | $Z^1$ | $Z^2$ | $Z^3$ | $\lambda_{max}$ [nm]* |
|---|---|---|---|---|
| 4 | 4-$C_6H_5$—N=N | 4,4'-(HN)(NH)-2,2,6,6-tetramethylpiperidine (CH₃ CH₃ / HN–NH \ CH₃ CH₃) | $CH_3CO$ | 511 |
| 5 | 4-$CH_3CO$—NH | piperazine (HN   N) | $CH_3CO$ | 502 |
| 6 | 4-$CH_3CO$—NH | $C_2H_5$—N   N (N-ethylpiperazine) | $CH_3CO$ | 503 |
| 7 | 4-$CH_3CO$—NH | $(CH_3)_2N-C_2H_4-NH$ | $CH_3CO$ | 504 |
| 8 | 2-$CH_3O$ | $(CH_3)_2N-C_2H_4-NH$ | $CH_3CO$ | 502 |
| 9 | 4-$CH_3CO$—NH | $H_2N-CH_2C(CH_3)_2CH_2-NH$ | $CH_3CO$ | 502 |
| 10 | 4-$CH_3CO$—NH | $H_2N-CH(CH_3)CH_2-NH$ | $C_2H_5CO$ | 502 |
| 11 | 4-$CH_3CO$—NH | $H_2N-CH(CH_3)CH_2-NH$ | $i\text{-}C_3H_7CO$ | 502 |
| 12 | 4-$CH_3CO$—NH | CH₃ CH₃ / HN–NH \ CH₃ CH₃ | $CH_3CO$ | 503 |
| 13 | 2-$CH_3O$ | CH₃ CH₃ / HN–NH \ CH₃ CH₃ | $CH_3CO$ | 503 |
| 14 | 4-$CH_3CO$—NH | $H_2N-C_3H_6-NH$ | $CH_3CO$ | 501 |
| 15 | 2-$CH_3O$ | $H_2N-C_2H_4-NH-C_2H_4-NH$ | $CH_3CO$ | 504 |
| 16 | 4-$CH_3CO$—NH | cyclohexyl-NH—$C_3H_6$—NH | $CH_3CO$ | 503 |
| 17 | 4-$CH_3CO$—NH | HN   N—NH—$C_2H_4$—NH | $CH_3CO$ | 502 |
| 18 | 4-$CH_3CO$—NH | $H_2N-C_2H_4-NH-C_2H_4-NH$ | $CH_3CO$ | 498 |

*measured in 85% strength by weight acetic acid

EXAMPLE 20

8.2 g (0.05 mol) of N-acetyl-N-methyl-p-phenylenediamine were dissolved in a mixture of 100 g of ice, 125 ml of 30% strength by weight hydrochloric acid and 12.5 ml of water. The addition of 12.5 g of ice was followed at 0°–5° C. by the addition of 15 ml of 23% strength by weight aqueous sodium nitrite solution, after which the mixture was stirred at 0°–5° C. for a further hour and then clarified.

The resulting solution of the diazonium salt was reacted with an equimolar amount of sulfonamide as described in Example 1.

Filtration with suction and drying yielded 17 g (66%) of the dye of the formula

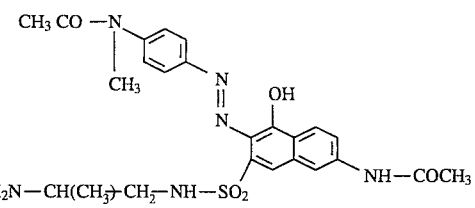

λmax: 488 nm (in 85% strength by weight acetic acid)

EXAMPLE 21

382 g (1.6 mol) of J-acid were dissolved in 1000 g of water and 1000 g of acetone and the solution was adjusted to pH 7 with 90 ml of 50% strength by weight sodium hydroxide solution. 339 g (3 mol) of chloroacetyl chloride were added dropwise at 0°–5° C. over 3 h, during which the pH was maintained at 6.1 with 20% strength by weight aqueous sodium carbonate solution. Then the acetone and water were distilled off under reduced pressure to leave a residual volume of 1000 ml. After 500 ml of water had been added, a pH of 2.7 was set with concentrated hydrochloric acid, and the precipitated chloroacetyl-J-acid was isolated.

66.8 g (0.2 moil) of the chloroacetyl-J-acid obtained as described above were added to 104 ml of phosphoryl chloride and 40 ml of N,N-dimethylacetamide at 25°–30° C. and left at that temperature for a further 18 h.

After precipitation in ice-water the sulfonyl chloride was isolated, taken up in ethyl acetate, dried over sodium sulfate and evaporated to dryness in a rotary evaporator.

13.4 g (0.04 mol) of chloroacetyl-J-acid chloride were added at 25°–30° C. to 50 g of ethanolamine, and the mixture was stirred at room temperature for 18 h, then poured onto 250 g of ice and adjusted to pH 7.5 with 70 g of 30% strength by weight hydrochloric acid. The solution was coupled with 0.04 mol of diazotized p-aminoacetanilide as described in Example 1.

Yield: 18.2 g (82%) of the dye of the formula

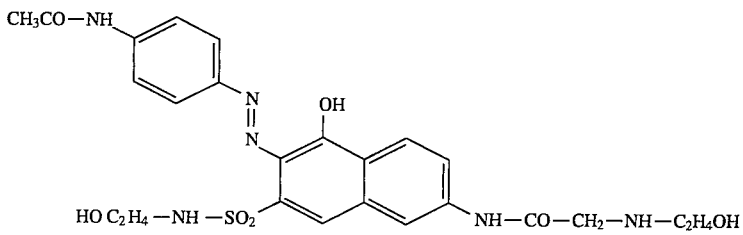

$\lambda$max: 488 nm (in 85% strength by weight acetic acid)

EXAMPLE 22

16.7 g (0.05 mol) of chloroacetyl-J-acid chloride were added at 25°–30° C. to 60 g of 1,2-diaminopropane, and the mixture was stirred at room temperature for 18 h, then poured onto 250 g of ice and adjusted to pH 7.5 with 70 g of 30% strength by weight hydrochloric acid. The solution was coupled with 0.05 mol of diazotized p-aminoacetanilide as described in Example 1.

Yield: 17 g (54%) of the dye of the formula

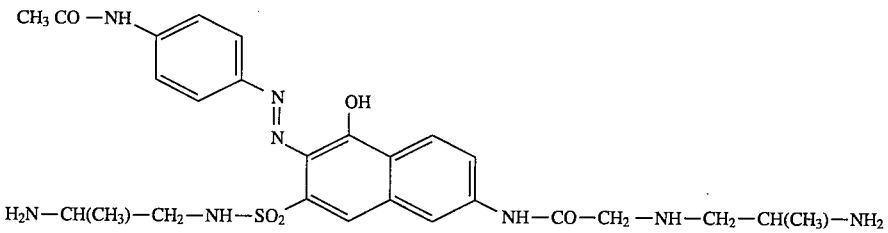

$\lambda$max: 499 nm (in 85% strength by weight acetic acid)

EXAMPLE 23

20 g (0.2 mol) of succinic anhydride were dissolved in 50 g of N,N-dimethylacetamide and admixed at 50° C. with 23.8 g (0.1 mol) of J-acid. After a further 1.5 h at 70° C. the mixture was cooled down to 30° C., admixed with 76.7 g (0.5 mol) of phosphoryl chloride and stirred at room temperature for 18 h. The sulfonyl chloride was isolated by hydrolysis in ice-water, filtering with suction and subsequent takeup of the filter residue in ethyl acetate. Drying over sodium sulfate and removing the solvent under reduced pressure yielded 31.5 g (93%) of the sulfonyl chloride.

The sulfonyl chloride was first converted into the amide and then into the dye, both steps being carried out as described in Example 1.

Salting out yielded 40.3 g (99%) of the dye of the formula

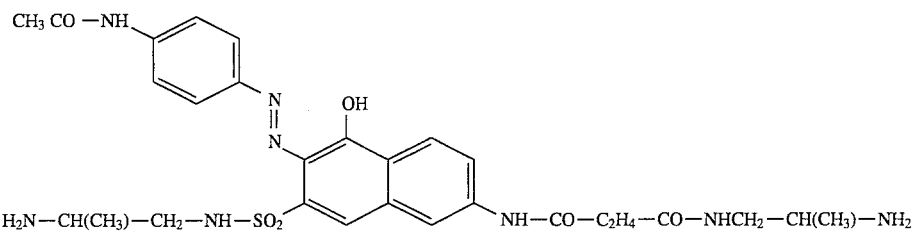

λmax: 502 nm (in 85% strength by weight acetic acid)

EXAMPLE 24

31.5 g of the sulfonyl chloride of Example 23 were dissolved in 270 ml of xylene and 75 ml of N-cyclohexylpyrrolidone and added dropwise at 40° C. to 35.2 g (0.4 mol) of N,N-dimethyl-1,2-ethylenediamine. After a further 2 h at from 40° to 45° C. the reaction had ended. The sulfonamide was transferred to the aqueous phase by stirring with 55 g of glacial acetic acid and 25 g of water, and separated off.

The aqueous phase was admixed at pH 5 with 0.08 mol of the diazotized p-aminoacetanilide of Example 1. The pH was kept constant by addition of aqueous sodium carbonate solution.

Salting out with sodium chloride yielded the dye of the formula

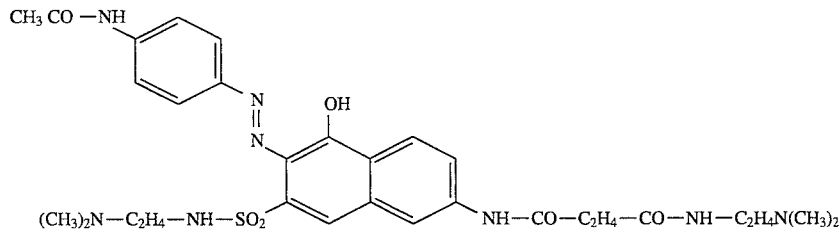

λmax: 498 nm (in 30% strength by weight acetic acid)

EXAMPLE 25

Example 24 was repeated except that the sulfonyl chloride was admixed at 20° C. with 70 g (0.8 mol) of N,N-dimethyl-1,2-ethylenediamine and stirred at room temperature for 60 h. The resulting oil was admixed with 100 ml of water, brought to pH 5 with hydrochloric acid and then further reacted as described.

The same method gives the dyes of the formula

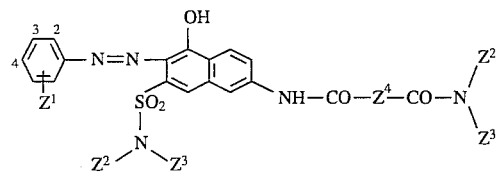

listed below in Table 2. (Column 3 thereof indicates in each case the amine $HNZ^2Z^3$ used in the reaction.)

TABLE 2

| Ex. No. | $Z^1$ | $HNZ^2Z^3$ | $Z^4$ | $\lambda_{max}$ [nm]* |
|---|---|---|---|---|
| 26 | 4-NHCOCH$_3$ | H$_2$N(CH$_2$)$_3$N(C$_2$H$_5$)$_2$ | CH$_2$CH$_2$ | 498 |
| 27 | 4-NHCOCH$_3$ | H$_2$N(CH$_2$)$_3$NH(CH$_2$)$_3$NH$_2$ | CH$_2$CH$_2$ | 498 |
| 28 | 4-NHCOCH$_3$ | HN⌒NH (piperazine) | CH$_2$CH$_2$ | 500 |
| 29 | 4-NHCOCH$_3$ | H$_2$N(CH$_2$)$_2$NH$_2$ | CH$_2$CH$_2$ | 496 |
| 30 | 4-NHCOCH$_3$ | H$_2$N(CH$_2$)$_3$NH$_2$ | CH$_2$CH$_2$ | 498 |
| 31 | 4-NHCOCH$_3$ | H$_2$N(CH$_2$)$_4$NH$_2$ | CH$_2$CH$_2$ | 498 |
| 32 | 2-OCH$_3$ | H$_2$N(CH$_2$)$_2$NH$_2$ | CH$_2$CH$_2$ | 498 |
| 33 | 2-OCH$_3$ | H$_2$N(CH$_2$)$_3$NH$_2$ | CH$_2$CH$_2$ | 496 |
| 34 | 2-OCH$_3$ | H$_2$N(CH$_2$)$_4$NH$_2$ | CH$_2$CH$_2$ | 500 |
| 35 | 2-OCH$_3$ | H$_2$N(CH$_2$)$_3$NH(CH$_2$)$_3$NH$_2$ | CH$_2$CH$_2$ | 498 |

*measured in 30% strength by weight acetic acid

We claim:
1. A dye of the formula I

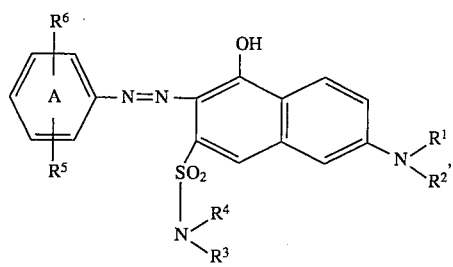

where the ring A may be benzofused, $R^1$ is $C_1$-$C_{13}$-alkyl, benzyl, 2-chloroethyl, substituted or unsubstituted phenyl, $C_1$-$C_8$-alkanoyl, substituted or unsubstituted benzoyl or a radical of the formula

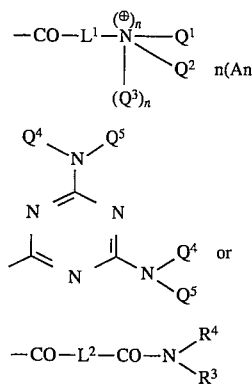

where $L^1$ is $C_1$-$C_3$-alkylene, $L^2$ is $C_2$-$C_3$-alkylene, which may be chlorine-substituted, vinylene or phenylene, n is 0 or 1, $Q^1$, $Q^2$ and $Q^3$ are identical or different and each is independently of the others hydrogen or unsubstituted or hydroxyl-substituted $C_1$-$C_8$-alkyl, which may be interrupted by from 1 to 3 oxygen atoms in ether function or by from 1 to 3 imino groups which imino groups may be substituted by $C_1$-$C_4$-alkyl or ω-hydroxy-$C_1$-$C_8$-alkyl, which may be interrupted by from 1 to 3 oxygen atoms in ether function, or $Q^1$ and $Q^2$, together with the nitrogen atom joining them together, are a 5- or 6-membered saturated or unsaturated heterocyclic radical which may contain a further hetero atom selected from the group consisting of nitrogen, oxygen and sulfur, and $An^\ominus$ is the equivalent of an anion, and $Q^4$ and $Q^5$ are identical or different and each is independently of the other (1) $C_1$-$C_{13}$-alkyl, which may be interrupted by from 1 to 4 oxygen atoms in ether function, by imino or by $C_1$-$C_4$-alkyl-imino groups and which $C_1$-$C_{13}$-alkyl, interrupted or not interrupted, may be substituted by amino, by a 5- or 6-membered saturated or unsaturated heterocyclic radical which contains a nitrogen atom and may contain a further hetero atom selected from the group consisting of nitrogen, oxygen and sulfur, or by substituted or unsubstituted $C_5$-$C_7$-cycloalkyl, (2) substituted or unsubstituted phenyl, (3) substituted or unsubstituted $C_5$-$C_7$-cycloalkyl or (4) unsubstituted or $C_1$-$C_4$-alkyl-substituted piperidinyl, and $Q^4$ may also be hydrogen.

$R^2$ is hydrogen or $C_1$-$C_4$-alkyl or $R^1$ and $R^2$ together are a radical of the formula CO—$L^3$, where $L^3$ is $C_3$-$C_4$-alkylene, $R^3$ and $R^4$ are identical or different and each is independently of the other (1) $C_1$-$C_{13}$-alkyl, which may be interrupted by from 1 to 4 oxygen atoms in ether function or by from 1 to 4 imino groups which imino groups may be substituted by $C_1$-$C_4$-alkyl or ω-hydroxy-$C_1$-$C_8$-alkyl, which may be interrupted by from 1 to 3 oxygen atoms in ether function, and which $C_1$-$C_{13}$-alkyl, interrupted or not interrupted, may be substituted by hydroxyl, by amino, by a 5- or 6-membered saturated or unsaturated heterocyclic radical which contains a nitrogen atom and may contain a further hetero atom selected from the group consisting of nitrogen, oxygen and sulfur, or by substituted or unsubstituted $C_5$-$C_7$-cycloalkyl, (2) substituted or unsubstituted phenyl, (3) substituted or unsubstituted $C_5$-$C_7$-cycloalkyl or (4) unsubstituted or $C_1$-$C_4$-alkyl-substituted piperidinyl, and $R^3$ may also be hydrogen, and $R^3$ and $R^4$, together with the nitrogen atom joining them together, ar a 5- or 6-membered saturated heterocyclic radical which may contain a further hetero atom selected from the group consisting of oxygen and sulfur, $R^5$ is hydrogen, $C_1$-$C_4$-alkyl, $C_1$-$C_4$-alkoxy, $C_2$-$C_5$-alkanoylamino, halogen, nitro, cyano, unsubstituted or $C_1$-$C_4$-alkyl-substituted phenylazo or a radical of the formula

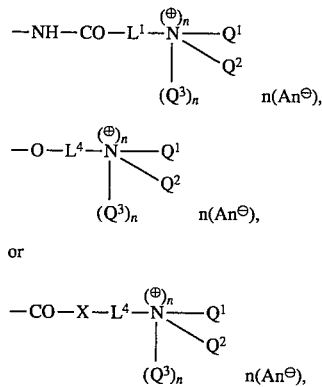

where X is oxygen or imino, and $L^4$ is $C_2$-$C_4$-alkylene, and $Q^1$, $Q^2$, $Q^3$, n and $An^\ominus$ are each as defined above, and $R^6$ is hydrogen, $C_1$-$C_4$-alkyl, $C_1$-$C_4$-alkoxy, halogen, nitro, or cyano, with the proviso that at least one quaternizable or quaternary group is present in the molecule.

2. A dye as claimed in claim 1, wherein $R^1$ is $C_2$-$C_4$-alkanoyl, benzoyl or a radical of the formula

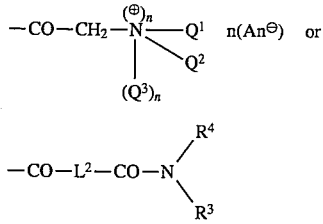

where $L^2$, $Q^1$, $Q^2$, $Q^3$, $R^3$, $R^4$, $An^\ominus$ and n are each as defined in claim 1, and $R^2$ is hydrogen, $C_1$-$C_4$-alkyl or phenyl.

3. A dye as claimed in claim 1, wherein $R^3$ is hydrogen and $R^4$ is $C_1$-$C_{13}$-alkyl which is interrupted by 1 or 2 oxygen atoms in ether function, imino or $C_1$-$C_4$-alkylimino groups and/or substituted by amino or by a 5- or 6-membered saturated or unsaturated heterocyclic radical which contains one or two nitrogen atoms.

4. A dye as claimed in claim 1, wherein $R^5$ is $C_1$-$C_4$-alkyl, $C_1$-$C_4$-alkoxy, $C_2$-$C_4$-alkanoylamino or phenylazo and $R^6$ is hydrogen.

5. A method for dyeing or printing polymeric material, which comprises applying thereto a dye as claimed in claim 1.

* * * * *

Disclaimer 5,571,898—Ulrike Schloessner, Ludwigshafen; Udo Mayer, Frankenthal, both of Germany. BASIC DYES BASED ON AMIDES OF J-ACID (1-HYDROXY-6-AMINONAPHTHALENE-3-SULFONIC ACID) AND AMIDES OF J-ACID. Patent dated November 5, 1996. Disclaimer filed September 9, 1997, by the assignee, BASF Aktiengesellschaft.

Hereby enters this disclaimer to the entire term of said patent.
*(Official Gazette,* November 4, 1997)